(12) United States Patent
Willis et al.

(10) Patent No.: US 6,960,184 B2
(45) Date of Patent: Nov. 1, 2005

(54) INJECTION DEVICES

(75) Inventors: John Willis, Shirley, MA (US); Thaddeus Minior, Berlin, MA (US); Robert Gonnelli, Mahwah, NJ (US)

(73) Assignee: Biovalve Technologies, Inc., N. Grafton, MA (US)

( * ) Notice: Subject to any disclaimer, the term of this patent is extended or adjusted under 35 U.S.C. 154(b) by 97 days.

(21) Appl. No.: 10/175,541

(22) Filed: Jun. 18, 2002

(65) Prior Publication Data
US 2004/0249339 A1 Dec. 9, 2004

Related U.S. Application Data

(63) Continuation of application No. 09/465,573, filed on Dec. 17, 1999, now Pat. No. 6,406,455.
(60) Provisional application No. 60/255,144, filed on Dec. 14, 2000.

(51) Int. Cl.⁷ .......................... A61M 5/30; A61M 37/00
(52) U.S. Cl. .............................. 604/68; 604/69; 604/70; 604/90; 604/191
(58) Field of Search .............................. 604/140–145, 604/82, 89–92, 90, 91, 68–72, 87–88, 93.01, 125–126, 131–133, 181, 187, 191, 200, 218, 244

(56) References Cited

U.S. PATENT DOCUMENTS

| | | |
|---|---|---|
| 3,675,651 A | 7/1972 | Meyer |
| 3,802,430 A | 4/1974 | Schwebel et al. |
| 3,977,401 A | 8/1976 | Pike |
| 3,977,402 A | 8/1976 | Pike |
| 4,007,739 A | 2/1977 | Bron et al. |
| 4,031,889 A | 6/1977 | Pike |
| 4,089,334 A | 5/1978 | Schwebel et al. |
| 4,124,024 A | 11/1978 | Schwebel et al. |
| 4,177,810 A | 12/1979 | Gourlandt |
| 4,233,973 A | 11/1980 | Shukla |
| 4,265,241 A | 5/1981 | Portner et al. |
| 4,299,220 A | 11/1981 | Dorman |
| 4,338,980 A | 7/1982 | Schwebel et al. |
| 4,360,019 A | 11/1982 | Portner et al. |
| 4,539,005 A | 9/1985 | Greenblatt |
| 4,573,994 A | 3/1986 | Fischell et al. |
| 4,596,556 A | 6/1986 | Morrow et al. |
| 4,626,244 A | 12/1986 | Reinicke |
| 4,666,430 A | 5/1987 | Brown et al. |
| 4,692,151 A | 9/1987 | Blackman |
| 4,717,384 A | 1/1988 | Waldeisen |
| 4,741,737 A | 5/1988 | Meyer et al. |
| 4,773,900 A | 9/1988 | Cochran |
| 4,790,824 A | 12/1988 | Morrow et al. |
| 4,820,273 A | 4/1989 | Reinicke |
| 4,828,548 A | 5/1989 | Walter |
| 4,940,460 A | 7/1990 | Casey et al. |
| 4,941,880 A | 7/1990 | Burns |
| 4,944,726 A | 7/1990 | Hilal et al. |
| 4,966,581 A | 10/1990 | Landau |
| 5,024,656 A | 6/1991 | Gasaway et al. |

(Continued)

FOREIGN PATENT DOCUMENTS

| | | |
|---|---|---|
| EP | 0 331 855 | 8/1995 |
| WO | WO 95/24176 | 9/1995 |
| WO | WO 99/21609 | 5/1999 |
| WO | WO 00/10630 | 3/2000 |
| WO | WO 00/48654 | 8/2000 |
| WO | WO 01/05451 | 1/2001 |
| WO | WO 01/05452 | 1/2001 |
| WO | WO 01/13975 | 3/2001 |

Primary Examiner—Michael J. Hayes
Assistant Examiner—Catherine S. Williams
(74) Attorney, Agent, or Firm—Ropes & Gray LLP

(57) ABSTRACT

Injection devices, such as needleless injection devices, and methods of making the using the same are disclosed.

21 Claims, 7 Drawing Sheets

U.S. PATENT DOCUMENTS

| | | | |
|---|---|---|---|
| 5,041,094 | A | 8/1991 | Perego et al. |
| 5,061,242 | A | 10/1991 | Sampson |
| 5,062,834 | A | 11/1991 | Gross et al. |
| 5,064,413 | A | 11/1991 | McKinnon et al. |
| 5,088,983 | A | 2/1992 | Burke |
| 5,147,297 | A | 9/1992 | Myers et al. |
| 5,147,311 | A | 9/1992 | Pickhard |
| 5,163,909 | A | 11/1992 | Stewart |
| 5,176,645 | A | 1/1993 | Guerrero |
| 5,179,022 | A | 1/1993 | Sanford et al. |
| 5,184,450 | A | 2/1993 | Galy et al. |
| 5,224,936 | A | 7/1993 | Gallagher |
| 5,304,128 | A | 4/1994 | Haber et al. |
| 5,308,335 | A | 5/1994 | Ross et al. |
| 5,312,335 | A | 5/1994 | McKinnon et al. |
| 5,312,577 | A | 5/1994 | Peterson et al. |
| 5,383,851 | A | 1/1995 | McKinnon et al. |
| 5,399,163 | A | 3/1995 | Peterson et al. |
| 5,466,220 | A | 11/1995 | Brenneman |
| 5,480,381 | A | 1/1996 | Weston |
| 5,492,534 | A | 2/1996 | Athayde et al. |
| 5,499,972 | A | 3/1996 | Parsons |
| 5,503,627 | A | 4/1996 | McKinnon et al. |
| 5,503,628 | A | 4/1996 | Fetters et al. |
| 5,520,639 | A | 5/1996 | Peterson et al. |
| 5,527,288 | A | 6/1996 | Gross et al. |
| 5,531,683 | A | 7/1996 | Kriesel et al. |
| 5,549,561 | A | 8/1996 | Hjertman |
| 5,569,189 | A | 10/1996 | Parsons |
| 5,599,302 | A | 2/1997 | Lilley et al. |
| 5,607,418 | A | 3/1997 | Arzbaecher |
| 5,616,132 | A | 4/1997 | Newman |
| 5,618,269 | A | 4/1997 | Jacobsen et al. |
| 5,649,912 | A | 7/1997 | Peterson |
| 5,685,846 | A | 11/1997 | Michaels, Jr. |
| 5,693,017 | A | 12/1997 | Spears et al. |
| 5,704,911 | A | 1/1998 | Parsons |
| 5,730,723 | A | 3/1998 | Castellano et al. |
| 5,746,714 | A | 5/1998 | Salo et al. |
| 5,779,668 | A | 7/1998 | Grabenkort |
| 5,782,802 | A | 7/1998 | Landau |
| 5,814,020 | A | 9/1998 | Gross |
| 5,836,915 | A | 11/1998 | Steinbach et al. |
| 5,846,233 | A | 12/1998 | Lilley et al. |
| 5,851,198 | A | 12/1998 | Castellano et al. |
| 5,858,001 | A | 1/1999 | Tsals et al. |
| 5,860,957 | A | 1/1999 | Jacobsen et al. |
| 5,891,085 | A | 4/1999 | Lilley et al. |
| 5,891,086 | A | 4/1999 | Weston |
| 5,893,397 | A | 4/1999 | Peterson et al. |
| 5,938,637 | A | 8/1999 | Austin et al. |
| 5,957,895 | A | 9/1999 | Sage et al. |
| 5,971,953 | A | 10/1999 | Bachynsky |
| 5,993,412 | A | 11/1999 | Deily et al. |
| 6,045,534 | A | 4/2000 | Jacobsen et al. |
| 6,056,724 | A | 5/2000 | Lacroix |
| 6,063,053 | A | 5/2000 | Castellano et al. |
| 6,074,360 | A | 6/2000 | Haar et al. |
| 6,096,002 | A | 8/2000 | Landau |
| 6,099,504 | A | 8/2000 | Gross et al. |
| 6,132,395 | A | 10/2000 | Landau et al. |
| 6,165,155 | A | 12/2000 | Jacobsen et al. |
| 6,258,062 | B1 | 7/2001 | Thielen et al. |
| 6,258,063 | B1 | 7/2001 | Haar et al. |
| 6,319,224 | B1 | 11/2001 | Stout et al. |
| 6,319,225 | B1 | 11/2001 | Sugita et al. |
| 6,406,455 | B1 * | 6/2002 | Willis et al. .................. 604/68 |
| 2001/0027290 | A1 | 10/2001 | Weston |
| 2001/0027293 | A1 | 10/2001 | Joshi |

\* cited by examiner

INJECTION DEVICES

This is a divisional application of U.S. non-provisional application Ser. No. 09/465,573, filed on Dec. 17, 1999, now U.S. Pat. No. 6,406,455, which claims benefit from U.S. provisional application 60/112,805, filed on Dec. 18, 1998.

BACKGROUND OF THE INVENTION

The invention relates to injection devices and to methods of making and using the same.

SUMMARY OF THE INVENTION

In general, the invention features, an injection device. The injection device includes:

a gas chamber containing a gas or a source of gas;

a port which can allow for release of gas from said gas chamber;

a plunger, which upon the release of gas from said gas chamber, can cause movement of at least a first piston;

a first piston;

a second piston;

a first chamber, e.g. a chamber useful for drug storage and mixing;

a piston housing, in which are disposed said first piston, said second piston and said first chamber;

a displacement member which can, independent of the motive power of gas from said gas chamber, cause movement of one or both of the first and second pistons (the displacement member can be the plunger or a separate member);

an orifice suitable for needleless injection in communication with said first chamber;

wherein said first and second piston, are slideably disposed within said piston housing, and said displacement member, said source of gas, and said plunger are disposed such that:

in a first position of said pistons, a second chamber, e.g., a fluid reservoir, is defined within said piston housing by said first piston, said piston housing and said second piston, said displacement member can move one or both of said pistons into a second position wherein said first piston is in a position such that said second chamber, which can be a fluid reservoir, is in communication with said first chamber, which can be a drug storage and mixing chamber, and said second piston is moved in the direction of the first piston, thereby decreasing the volume of the second chamber and allowing the transfer of fluid from the second chamber to the first chamber, said plunger, upon release of gas from the gas chamber, causes the first piston to move so as to decrease the volume of the first chamber allowing a substance to be expelled through the orifice and from said chamber.

In a preferred embodiment the displacement member is activated manually.

In a preferred embodiment the displacement member is capable of incremental movement, e.g., manually activated incremental movement, of at least one of the pistons. By incremental is meant that the piston can be displaced a certain amount, that displacement can be halted, but can then be further displaced.

In a preferred embodiment a surface of the displacement member is in contact with a surface that is rigidly attached to the housing and friction between the two surfaces allows for incremental movement, e.g., manually activated incremental movement, of the displacement member with regard to the housing or of one of the pistons.

In a preferred embodiment a surface rigidly connected with the displacement member is in threaded contact with a surface that is rigidly connected with the piston housing and rotation between the two surfaces allows for incremental movement, e.g., manually activated incremental movement, of the displacement member with regard to the piston housing or of one of the pistons.

In a preferred embodiment, the housing includes a bypass, e.g., depressions in the wall of the housing, which when engaged by a piston, allows communication between the reservoir and drug storage and mixing chamber.

In a preferred embodiment the piston housing includes two subparts. In such embodiments one module, e.g., a storage and mixing or dry component module, can supply the first piston, first chamber, and a part of the piston housing and a second module occasionally, referred to herein as a second component, or liquid component, module, can supply the second chamber, second piston, and a part of the piston housing.

The first, module can include a first module housing, the first piston described above, a first module seal, and a first chamber defined by the first module housing said first piston' and optionally' the first module seal.

The second component module can include a second component module housing, the second piston referred to above, a second module seal, and a second chamber defined by the second module housing, the second piston, and the second module seal.

In a preferred embodiment the modules include threads, components or a bayonet closure, a storage module member and a fluid module member which present frictional resistance to disengagement, or other means for holding the two modules together.

In a preferred embodiment engagement of the first module with the second module enables communication between the first chamber, and the second chamber.

In a preferred embodiment the first module includes a bypass, e.g., a bypass which allows fluid to travel around or through the storage module piston. In a particularly preferred embodiment, the first module housing includes a groove or passage which allows communication with the second module. In another embodiment the first piston includes a hole (which can include a valve) which allows communication between the second and first chambers.

In a preferred embodiment one or both modules includes a piercing member for piercing one or both of the first module and second module seals. One or both of the seals can be disposed such that upon engagement of the second module with the first, one or both of the seals are pierced. This can enable communication between the first and second chambers.

A piercing member can engage one or both seals when the modules are brought into close proximity and/or alignment. In a preferred embodiment, a piercing member can cut one or both seals as the threads or other engaging members of the modules are brought into contact or otherwise operated. In a preferred embodiment a piercing member cuts by rotation of a seal relative to a piercing member. In another embodiment the piercing member cuts by axial movement of a piercing member relative to a seal. The cut made by a piercing member should be such that small fragments of seal, which could enter the fluid chamber, are not formed.

Free portions of seal should be of a size and location such that they do not enter the first chamber. In one embodiment, rotational motion of a piercing member relative to a seal can produce a cut portion or fragment of the seal which is blocked by the first piston from entering the first chamber. In another embodiment one or more portions or fragments of the seal remain attached to the housing after piercing.

In another embodiment, one or both seals are pierced by axial displacement of one or both pistons.

In another aspect, the invention, features a method of making an injection device having disposed therein a substance, e.g., a drug, e.g., a lyophilized protein. The method includes:

providing the drug storage and mixing chamber of an injection device described herein;

and depositing the drug in the storage and mixing chamber.

In preferred embodiments the drug is lyophilized in situ in the drug in the storage and mixing chamber.

In preferred embodiments the storage and mixing chamber is provided as part of a first module, and an operation, e.g., filling or lyophilization, is performed: with the rest of the elements of the injection device described herein present; without at least one of the other elements described herein, e.g., without the gas chamber present, or without at least one, or both, pistons present.

In preferred embodiments the storage and mixing chamber is provided as part of a first module, and an operation, e.g., filling or lyophilization, is performed without at least one of the other elements described herein, e.g., without the gas chamber present, or without at least one, or both, pistons present, and that element is added after the operation.

In preferred embodiments the liquid chamber is provided as part of a second module, and an operation, e.g., filling or sterilization, is performed: with the rest of the elements of the injection device described herein present; without at least one of the other elements described herein, e.g., without the gas chamber present, or without at least one, or both, pistons present.

In preferred embodiments the liquid chamber is provided as part of a second module, and an operation, e.g., filling or sterilization, is performed without at least one of the other elements described herein, e.g., without the gas chamber present, or without at least one, or both, pistons present, and that element is added after the operation.

In preferred embodiments, after deposit or lyophilization , one or more moisture resistant seals, e.g., a metal or polymer seat, are applied to the storage and mixing chamber.

In another aspect, the invention features, a piston housing having two subparts, for use with an injection device. The piston housing includes two modules: a first module which can contain a first substance, e.g., preferably a substance other than a liquid, e.g., a solid, e.g., a dry or lyophilized protein; and a second module, which can contain a second substance, e.g., a fluid or solute.

The first module, which can, e.g., be a storage and mixing module, can include a first module housing, a first module piston, e.g., the first piston described elsewhere herein, a first module seal, and a first chamber defined by the first module housing, said first piston, and the first module seal.

The second module can include a second module housing, a piston, e.g., the second piston referred to elsewhere herein, a second module seal, and a second chamber defined by the second module housing, the piston, and optionally the second module seal.

In a preferred embodiment the modules include threads, components or a bayonet closure, a first module member and a second module member which present frictional resistance to disengagement, or other means for holding the modules together.

In a preferred embodiment engagement of the second module with the first module enables communication between the second chamber and the first chamber.

In a preferred embodiment the first module includes a bypass, e.g., a bypass which allows fluid (e.g., from the second module chamber) to travel around or through the first module piston. In a particularly preferred embodiment, the first module housing includes a groove or passage which allows communication with the second module. In another embodiment the first piston includes a hole (which can include a valve) which allows communication between the second and first chambers.

In a preferred embodiment one or both modules includes a piercing member for piercing one or both of the first module and second module seals. One or both of the seals can be disposed such that upon engagement of the second module with the first, module, one or both of the seals are pierced. This can enable communication between the first and second chambers.

A piercing member can engage one or both seals when the modules are brought into close proximity and/or alignment. In a preferred embodiment, a piercing member can cut one or both seals as the threads or other engaging members of the modules are used to engage the modules. In a preferred embodiment a piercing member cuts by rotation of a seal relative to a piercing member. In another embodiment the piercing member cuts by axial movement of a piercing member relative to a seal. The cut made by a piercing member should be such that small fragments of seal, which could enter the fluid chamber, are not formed. Free portions of seal should be of a size and location such that they do not enter the first chamber. In one embodiment, rotational motion of a piercing member relative to a seal can produce a cut portion or fragment of the seal which is blocked by the first piston from entering the first chamber. In another embodiment one or more portions or fragments of the seal remain attached to the housing after piercing.

In another embodiment, one or both seals are pierced by axial displacement of one or both pistons.

In preferred embodiments the storage and mixing chamber is provided as part of a first module, and an operation, e.g., filling or lyophilization, is performed: with the rest of the elements of the piston housing present; without at least one of the other elements described herein, e.g., without the second module.

In preferred embodiments the liquid chamber is provided as part of a second module, and an operation, e.g., filling or sterilization, is performed: with the rest of the elements of the piston housing present; without at least one of the other elements described herein, e.g., without the first module.

In preferred embodiments, after deposit or lyophilization, one or more moisture resistant seals, e.g., a metal or polymer seal, are applied to the storage and mixing chamber.

The invention also features a method of providing a first and second component by providing the components in the modules described herein.

The invention also features a kit which includes one or more of: one or both of the modules described herein, e.g., a storage module containing a first component, e.g., a dry component, and/or a fluid module containing a second component, e.g., a diluent; instructions for use, and other elements of the injectable device described herein.

In order to reconstitute a drug disposed within a syringe many current designs of bypass syringes require that the patient to push the syringe piston forward in order to initiate flow of diluent into the lower part of the syringe containing the lyophilized drug. There is a certain amount of friction (sticksion) to be overcome in order to move the butyl rubber piston forward. Unless the patient has very good manual dexterity (which is not always the case) it is natural to apply too much pressure on the syringe piston. This action may lurch the piston forward which may result in overflow of diluent and drug out the end of the syringe. The syringes described herein minimize this problem.

Syringes disclosed herein, having two separate chambers which by mechanical means (e.g., threaded mating parts) provides a more foolproof action, with a mechanical advantage, that overcomes the sticksion problem.

The modular chamber-containing elements of the invention allow for flexible manufacturing, distribution, and use of medications which require mixing of two components.

Other features and advantages of the invention will be apparent from the following detailed description, and from the claims.

DETAILED DESCRIPTION

Drawings

The drawings are first briefly described.

NEEDLELESS SYRINGE

Figure 1:
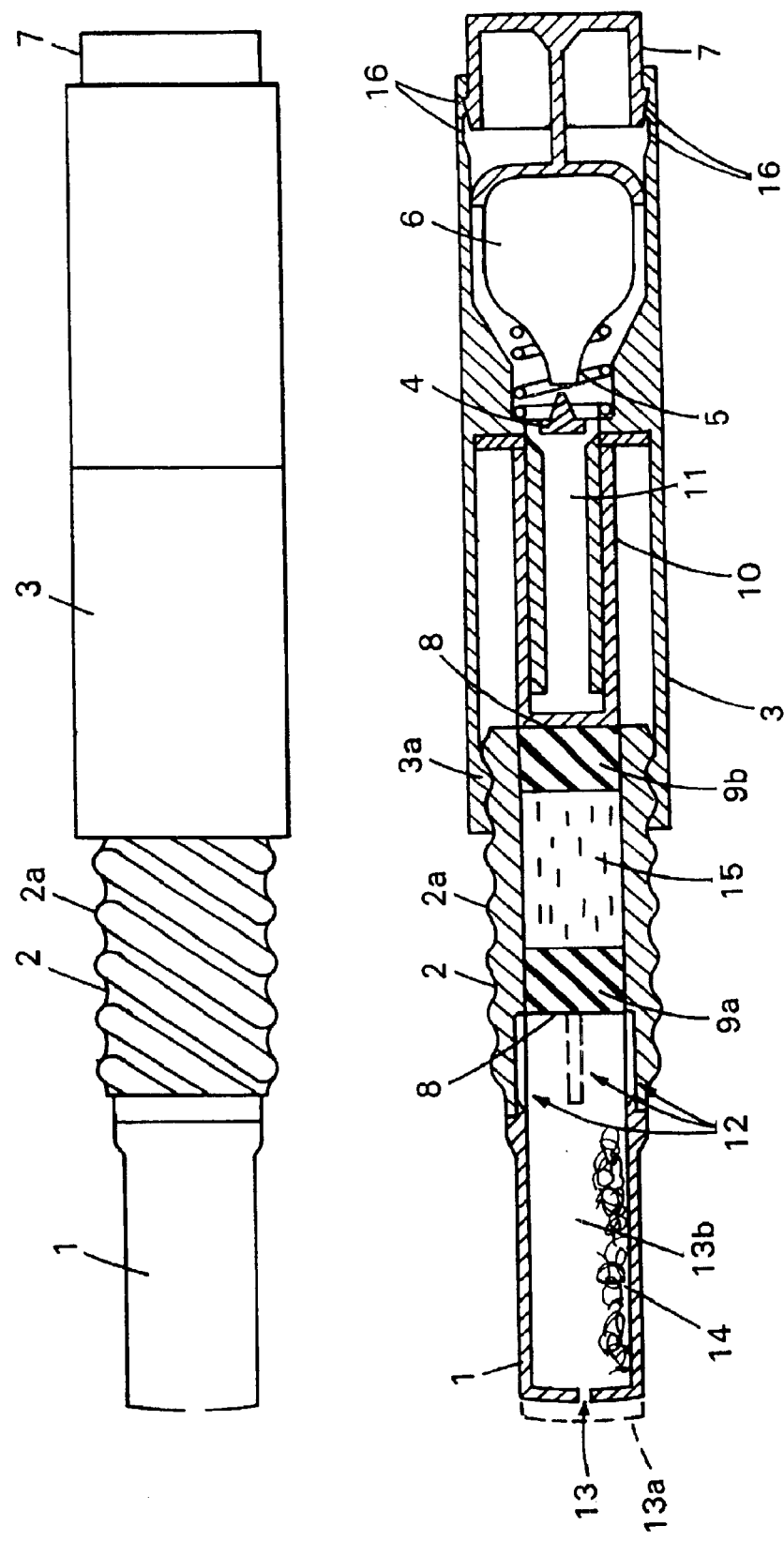
FIG. 1 is a diagram of an embodiment of an injectable device.

Referring to FIG. 1, an embodiment of a syringe includes three sections herein referred to as lower (1), middle (2), and upper (3). With the exception of the moisture resistant, e.g., metal foil, seals, spring (5) and compressed gas reservoir (6), all the other parts can be manufactured by plastic injection molding.

The lower section includes cylindrical housing (1), further defined by orifice (13), cap 13a, and one or a plurality, e.g., three or four, evenly spaced grooves (12) on the inside of (1) at the end facing piston 9a. The space (13b) within (1) is reserved for lyophilized drug (14).

The middle section is characterized by cylindrical housing (2) having an exterior thread (2a) and is further defined by a fluid reservoir (15) containing an aqueous diluent 15a). Fluid reservoir (15) is bounded by two pistons, e.g., rigid pistons having elastomeric seals or elastomeric pistons (9a, b) having metal foil seals on the outside aspect of housing (2).

Housing (2) may be manufactured separately from housing (1) such that it can be further characterized by a vapor deposited metal film on its outer surface. (Vapor barrier metalization is desirable if the material does not have a suitable vapor transmission characteristics.) Housing (1) and (2) must be securely mated at the time of assembly. This 2-part assembly allows for visual inspection of the mixing of diluent (15a) with lyophilized drug (14) while at the same time providing a vapor transmission barrier around the contained diluent (15). The metallized vapor barrier consisting of the metal foil seals on the outer ends of plungers (9a,b) and the coating on the outside of housing (2) will aid in ensuring a long shelf-life for the product. In addition to glass, metal foils and coatings offer the best protection against water vapor transmission. Since the syringe assembly will be packaged in a foil pouch, any water vapor escaping from the diluent reservoir will accumulate within the air inside the foil pouch. This accumulated water vapor may have an adverse effect on the stability of the lyophilized drug. This can be prevented or greatly reduced by the all encompassing metal barrier surrounding diluent reservoir (15).

The upper section includes cylindrical housing (3) having floating plunger (10), a space (11), fixed actuator (4), spring (5), compressed gas reservoir (6), release button (7) and detents (16). Housing (3) is further characterized by a thread (3a) on the inside of the housing which mates with that (2a) on the outside of middle section (2).

Figure 2:
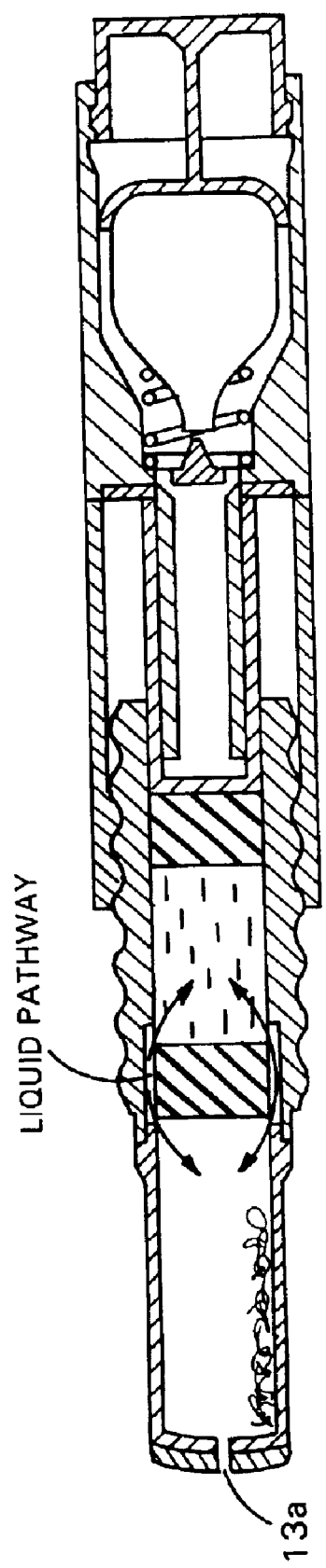
FIG. 2 is a diagram of an embodiment of an injectable device.
Figure 3:
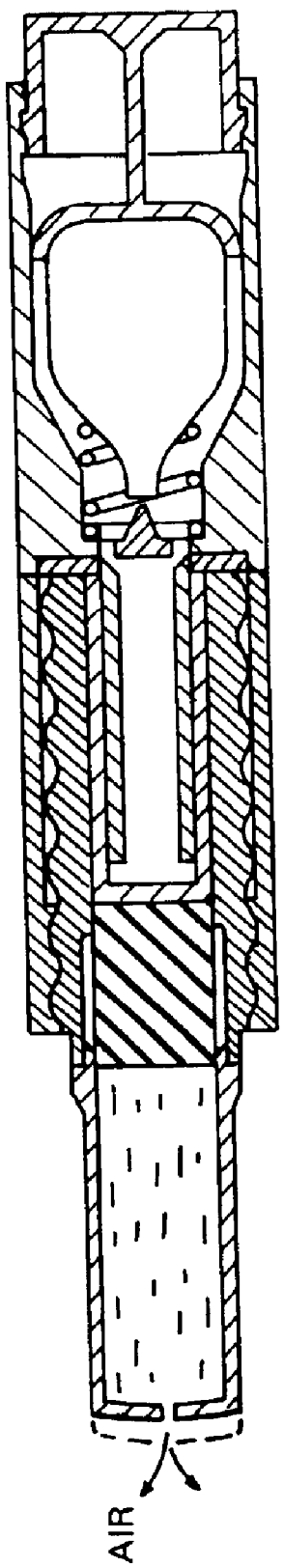
FIG. 3 is a diagram of an embodiment of an injectable device.
Figure 4:
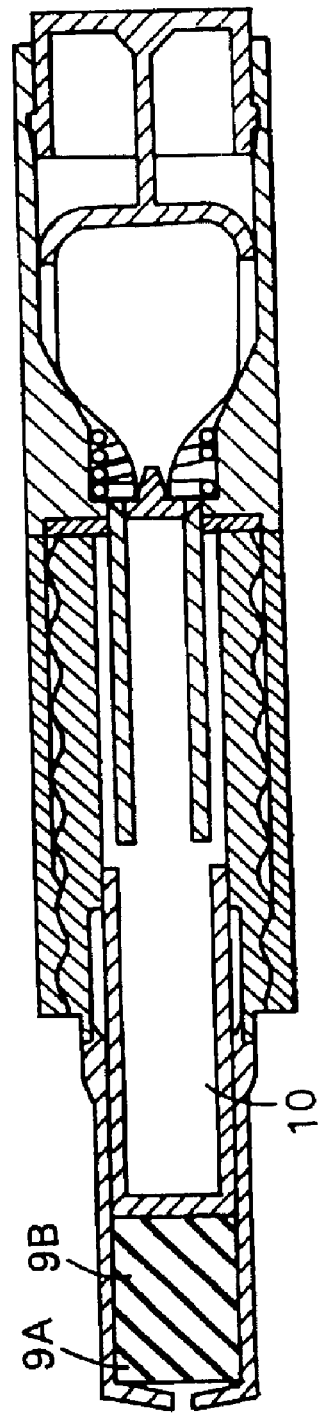
FIG. 4 is a diagram of an embodiment of an injectable device.

Referring to FIGS. 2, 3, and 4, use of the device is described. The device is removed from its foil pouch. The foil seal is removed from housing (1) and assembled with housing (2). (In some embodiments the foil seal is pierced automatically when the chambers are engaged.) Holding the syringe assembly in the vertical position with orifice 13 pointing up, grasp the lower section (2) (end facing up) with one hand and with the other rotate housing (3) around housing (2). This action results in floating plunger (10) pushing against plunger (9b) thereby pushing diluent column (15a) and plunger (9a) into the space defined by grooves (12). Pistons 9a and 9b are under radial compression. Since plunger (9a) is under compression when assembled, it expands when it enters the space surrounding grooves (12) thereby providing resistance to further movement. This is depicted in FIG. 2. The hydraulic coupling between the two pistons 9a and 9b is removed once the piston 9a is positioned with the grooves around it allowing the fluid to transfer to chamber (1). As housing (3) is further rotated, diluent (15a) flows by piston 9a through grooves (12) and into space (13b) containing lyophilized drug (14) until all the diluent is pushed into housing (1) at which time housing (3) reaches the end of its travel (e.g., approximately ¾ turn, the amount of rotation can vary, e.g., on the thread pitch selected). This is depicted in FIG. 3. The air displaced by diluent (15a) escapes through the hydrophobic vent in cap (13a). In this position piston 9a and 9b have made contact and jointly form a seal over the fluid transfer slots.

The syringe assembly is rocked in a back and forth motion until the drug is totally dissolved and thoroughly mixed with diluent (15a).

To inject the drug into the body, cap 13a is removed and while holding the syringe assembly in the vertical position, orifice 13 is pressed against the skin. The thumb is then used to press injection button (7). This action locks the button in position at detents 16, actuator (4) seats against the chamfered end of opening 11. When gas reservoir (6) hits the pointed end of the actuator (4), a seal is ruptured in reservoir (6) thereby releasing the compressed gas contained therein. The gas escapes through actuator (4) and into opening (11) where it impinges upon the bottom of floating plunger (10). Plunger (10) pushes against mated pistons (9a,b) (see FIG.

3) thereby expelling the drug through orifice 13 and into the skin. The entire injection process is complete less than 2 seconds. The final position of the pistons is depicted in FIG. 4. At this point, the injection is complete and the syringe is ready for disposal.

Actuator (4), radial slots (11a) and orifice (13) as well as the material surrounding and defining opening 11 can be designed so as to optimize the pressure profile. The interface between the outside surface of the fixed cylinder (11) and the inside plunger (10) can be configured to optimize the pressure profile during the injection phase. Devices in the art have used a variety of pressure profiles. While not wishing to be bound by a particular theory or approach, one potential profile can include an initial high-pressure spike. (−4000 psi) of very short duration (on the order of milliseconds) which creates a channel through the skin. The high-pressure spike is followed by a rapid fall in pressure to a constant level (−2,000 psi). This pressure is sufficient to keep the skin channel open and to allow for drug flow through the channel and into the body.

In another embodiment, the gas pressure can be generated by a chemical reaction similar to that found in automobile air bags. This chemical reaction is extremely fast and efficient and creates a source of high-pressure nitrogen gas.

As is discussed below, the chambers which hold the two substances can be provided by separate modules. The lower (1) and middle (2) sections of FIG. 1 can be replaced with the modular components described herein.

Modular Systems

Devices of the invention can include separate modules for a first component, e.g., a dry component, and a second component, e.g., a liquid component. The modules can be provided as two separate components and assembled, e.g., by the subject who will administer the component to himself or herself, or by another person, e.g., by an individual who provides or delivers health care. Together, the modules can form all or part of the piston housing of devices described herein. e.g., they can supply (1) the lower and middle (2) sections of FIG. 1. In such embodiments one module, referred to herein as a second component or liquid component module, can supply the second chamber, second piston, and a part of the piston housing, and a second module, referred to herein as a storage and mixing, or dry component module, can supply the first piston, first chamber, and a part of the piston housing. Although the description provided herein refers to a liquid component and a lyophilized or other dry component it will be understood that the methods and devices can be used to provide any first and second component where it is desirable to store or provide the components separately and combine them prior to administration to a subject.

Figure 5:
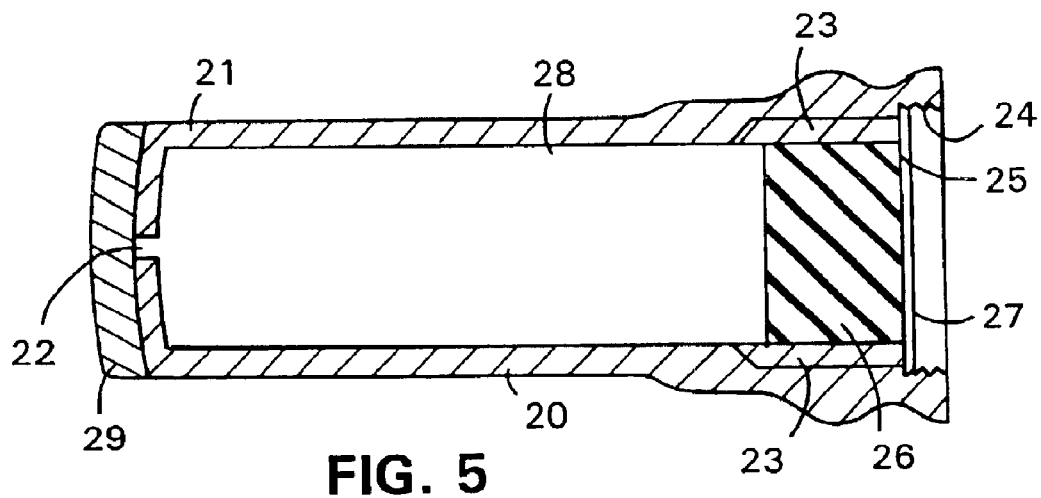
FIG. 5 is a diagram of an embodiment of a first module which can be used in a device described herein. The module includes a chamber which can be used to contain a dry component.

FIG. 5 is a diagram of an embodiment of a first module (20) which includes first module housing (21) having an orifice (22), fluid bypass passages (23), threads (24) for engagement with a second module, and a piercing element (25). Piston (26) is disposed within first module housing (20). First module seal (27) is disposed so as to prevent contact of the atmosphere with the chamber (28). Cap (29) covers orifice (22) and protects it until use. A dry substance, e.g., a lyophilized, protein can be disposed within chamber (28).

Figure 6:
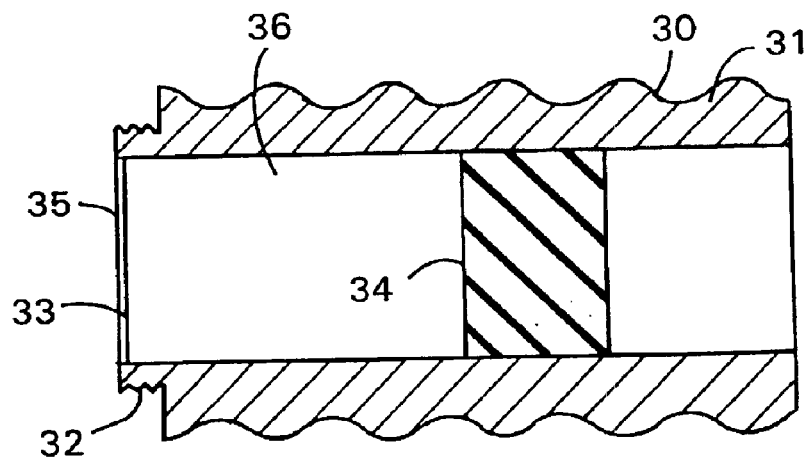
FIG. 6 is a diagram of an embodiment of a second module which can be used in a device described herein. The module includes a chamber which can be used to contain a liquid component.

FIG. 6 is a diagram of an embodiment of a second module (30) which includes second module housing (31), threads (32) for engagement with a first module, and a piercing element (33). Piston (34) is disposed on second module housing (30). Second module seal (35) is disposed so as to prevent contact of the atmosphere with the chamber (36). A liquid substance, e.g., a diluent or carrier, can be disposed within chamber (36).

Figure 7:
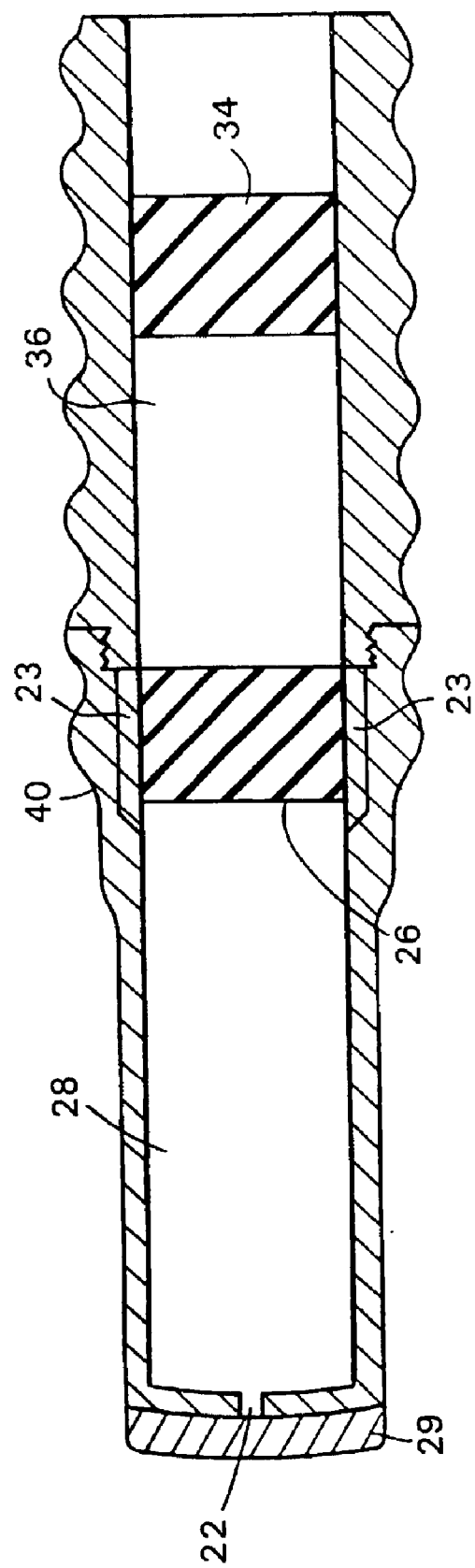
FIG. 7 is a diagram of an embodiment of a first module an embodiment of a second module in an engaged position.

FIG. 7 is a diagram of an embodiment of an assembled piston housing unit (40) which includes a first and second module. The assembled piston housing unit can be used with the injectors described herein. As shown, the engaged first and second module is then engaged with other components of the unit. However, assembly is not limited to this sequence, e.g., the second module can be combined with other elements and then engaged with the first module.

When the modules are incorporated into the assembled injector movement of second piston (34) in the direction of first piston (26) causes the contents of chamber (36) to enter chamber (28), by way of bypass (23). Travel of piston (26) so as to reduce the volume of chamber (28) results expulsion of the contents of chamber (28) through orifice (22).

In the embodiment described in FIG. 7, piston (26) is disposed such that it need not be moved relative to bypass (23) to allow communication of chamber (36) with chamber (28).

In other modular embodiments, piston (26) and bypass (23) are disposed analogous to the pistons shown in FIG. 1, i.e., disposed relative to one another such that piston (26) must be displaced to allow communications between chamber (36) and chamber (28).

Figure 8:
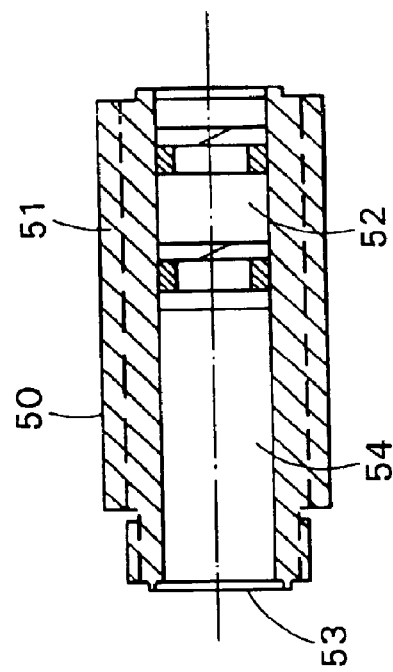
FIG. 8 is a diagram of an embodiment of a first module an embodiment of a second module.
Figure 8:
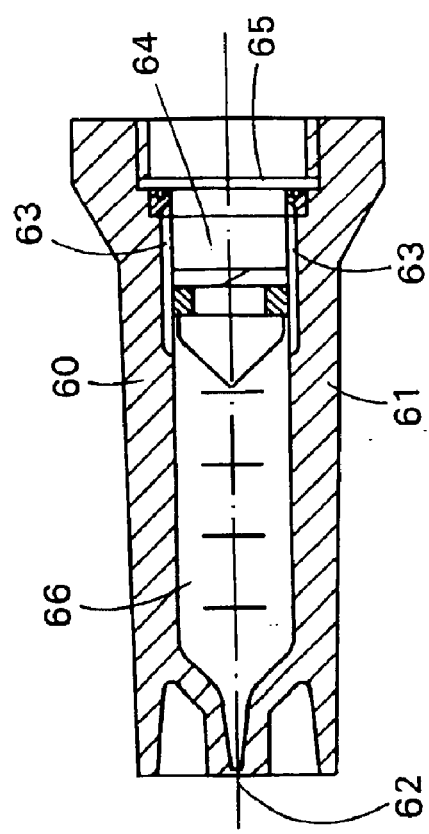
Figure 9:
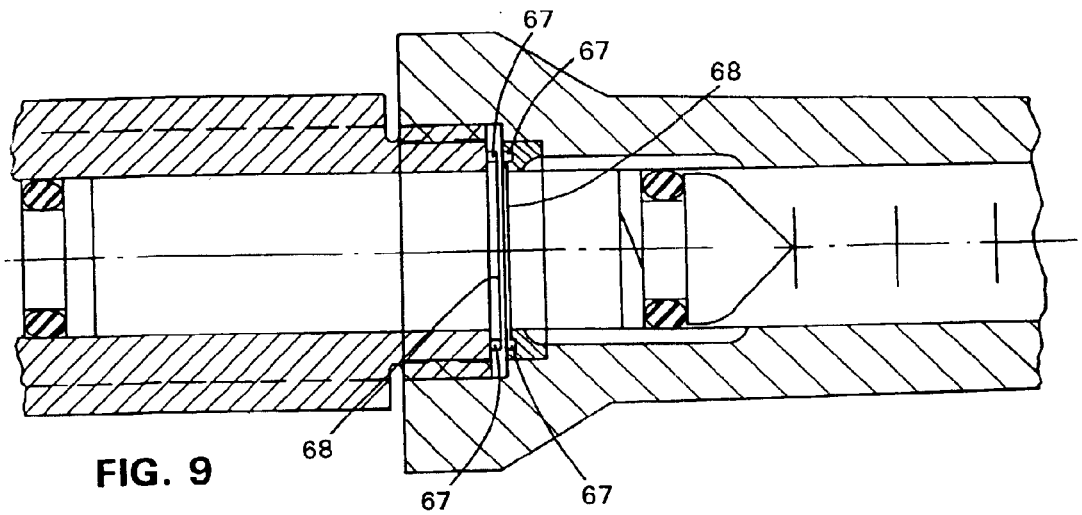
FIG. 9 is a diagram of an embodiment of a first module an embodiment of a second module in an initial phase of an engaged position.
Figure 10:
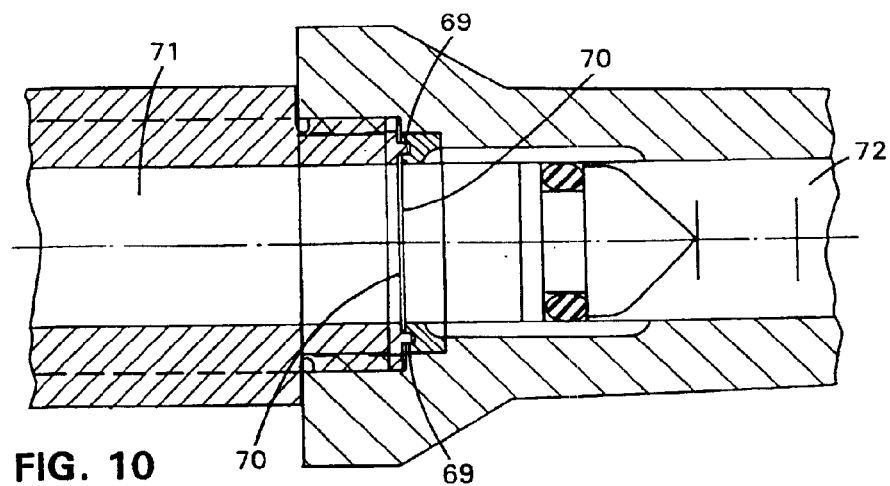
FIG. 10 is a diagram of an embodiment of a first module an embodiment of a second module in a completely engaged position.

FIGS. 8, 9, and 10 show another embodiment of a modular device.

FIG. 8 is a diagram of an embodiment of a first module (60) and second module (50). First module (60) includes first module housing (61) having an orifice (62), fluid bypass passages (63). Piston (64) is disposed within first module housing (60). First module seal (65) is disposed so as to prevent contact of the atmosphere with the chamber (66). A dry substance, e.g., a lyophilized protein can be disposed within chamber (66). Also shown is a second module (50) which includes second module housing (51) and piston (52) which is disposed in second module housing (50). Second module seal (53) is disposed so as to prevent contact of the atmosphere with the chamber (54). A liquid substance, e.g., a diluent or carrier, can be disposed within chamber (54).

FIG. 9 is a diagram of an embodiment of a first module an embodiment of a second module in an initial phase of an engaged position. Piercing elements (67) have not yet pierced seals (68).

FIG. 10 is a diagram of an embodiment of a first module an embodiment of a second module in a completely engaged position. Piercing elements (69) have pierced seals (70) allowing communication between chambers (71) and (72).

Operation of modular embodiments is otherwise analogous to that described for the embodiment shown in FIG. 1.

Use

The invention provides for the delivery of a mixture of two substances from the first chamber, a first substance originally held in the first chamber and a second substance originally held in the second chamber but transferred into the first by operation of the device. The first substance can be a dry substance, e.g., a lyophilized protein, nucleic acid, e.g., RNA or DNA, or polysaccharide. The first substance can be a vaccine, or a drug. The first substance can be a peptide, polypeptide, or protein, e.g., an antibody, an enzyme, a hormone or growth factor. Particularly preferred first substances include insulin.

The first substance can be: a blood protein, e.g., clotting factor VIII or a IX, complement factor or component; a hormone, e.g., insulin, growth hormone, thyroid hormone, a catecholamine, a gonadotrophin, PMSG, a trophic hormone, prolactin, oxytocin, dopamine and the like; a growth factor, e.g, EGF, PDGF, NGF, IGF's and the like; a cytokine, e.g., an, interleukin, CSF, GMCSF, TNF, TGF-alpha, TGF-beta. and the like; an enzyme, e.g., tissue plasminogen activator, streptokinase, cholesterol biosynthetic or degradative, glycosolases, and the like); a binding protein, e.g., a steroid binding protein, a growth hormone or growth factor binding protein and the like; an immune system protein, e.g., an antibody, SLA or MHC gene or gene product;an antigen, e.g., a bacterial, parasitic, or viral, substance or generally allergens and the like. The second substance can be a liquid, e.g., a diluent or solute. Such liquids can include buffers, inert fillers, pharmaceutically acceptable carriers, or the like.

The subject can be a human or an animal, e.g., a laboratory animal, or pet, e.g., a dog or cat, or other animal, e.g., a bovine, a swine, a goat, or a horse. The first and second substance can be combined by the subject, or by another person.

Formation of the Orifice

The size and shape of the orifice on the end of the syringe is important not only for obtaining the proper pressure profile, but also for minimizing or eliminating the possibility of protein shearing when using protein based drugs. This means the orifice must have a very smooth surface. Typically, shearing off a gate on the end of the syringe forms the orifice. This may result in a jagged edge, which can shear proteins. It is preferred to provide an orifice with edges which are sufficiently smooth such that protein shearing is minimized, e.g., an orifice sufficiently smooth such that after passage through the orifice in normal use a protein drug, e.g., insulin, retains at least, 40, 50, 60, 70, 80, 90, or 95% of a biological activity. A pin in the mold, or more preferably, laser machining, can be used to form the orifice. Laser machining, in particular, forms a very precise hole having a smooth surface.

Deposit of Drug

The lower section of the syringe (1 in drawing) can be used as a lyophilization chamber. Upon completion of lyophilization, a metal foil seal will be bonded over the end of chamber (1) where it mates with chamber (2). The end of chamber (2) will also have a bonded foil seal. The product will come in two or three parts. The user can remove the foil seals from chambers (1) and (2) and connect them together by means of a snap lock mechanism. In other embodiments the action of the chambers being connected will automatically shear the seals and contain them is a manner so as not to allow entry of portions of seal into the first chamber. The combined piece will then be threaded into the upper chamber (3) having the plunger means and actuator.

In modular embodiments, the drug is deposited in the storage chamber (see chamber (28) of FIG. 5 and FIG. 7). Other embodiments are within the following claims.

What is claimed is:

1. An injection device comprising:
   a housing having a proximate and a distal end;
   a first piston disposed in said housing near the proximate end and a second piston intermediate between said distal end and said first piston, said first and second piston independently moveable within the housing, said housing, second piston and first piston defining first and second chambers;
   an orifice suitable for needleless injection disposed on said distal end and in fluid communication with said first chamber;
   an actuator moveably attached to the said proximate end for moving at least said first piston toward said distal end so to open a fluid passageway between said first and second chambers; and
   a propellant disposed in said actuator and causing at least said first piston to expel a substance contained in at least said first chamber through said orifice.

2. The injection device of claim 1, wherein said actuator is activated manually.

3. The injection device of claim 2, wherein said actuator is capable of incremental movement relative to the housing.

4. The injection device of claim 1, wherein said actuator is attached to the housing by a threaded connection.

5. The injection device of claim 1, wherein said housing includes two subparts.

6. The injection device of claim 5, wherein said housing comprises:
   a first module comprising a first module housing, said first piston, a first module seal, and said first chamber defined by the first module housing, said first piston, and said first module seal; and
   a second module comprising a second module housing, said second piston, a second module seal, and said second chamber defined by said second module housing, said second piston, and said second module seal.

7. The injection device of claim 6, wherein engagement of said first module with said second module enables fluid communication between said first chamber and said second chamber.

8. The injection device of claim 6, wherein one or both modules comprises a piercing member for piercing one or both of the first module and second module seals.

9. The injection device of claim 6, wherein one or both of said module seals are disposed such that upon engagement of said first and second module, one or both of said seals are pierced.

10. A kit comprising one or more of one or both of the modules described in claim 6 wherein at least one of the modules contains a substance to be administered to a subject; and instructions for use.

11. The kit of claim 10, further comprising one or more one or more other elements of the injection device described in claim 1.

12. A method of making an injection device having disposed therein a substance, comprising:
   providing the injection device of claim 1;
   and depositing a drug in at least one of said first and second chamber.

13. The method of claim 12, wherein, a drug is lyophilized or sterilized in situ in said at least one chamber.

14. The method of claim 12, wherein, said at least one chamber is provided as part of a second module, and an operation is performed with the rest of the elements of the injection device described in claim 1 present.

15. The method of claim 12, wherein after an operation one or more moisture resistant seals are applied to the at least one chamber.

16. Method of providing a subject with a mixture of a first substance and a second substance comprising:
   providing the first substance in the first chamber and the second substance in the second chamber of the device described in claim 1;
   moving the actuator to mix the first substance with the second substance and
   administer the mixture to the subject.

17. The method of claim 16, wherein said first substance is a liquid and said second substance is a dry substance.

18. The method of claim 16 wherein said second substance is a protein.

19. The injection device of claim 1, wherein the actuator further comprises a plunger or a separate member that transfers movement to said first piston.

20. The injection device of claim 1, wherein the propellant is a pressurized gas.

21. The injection device of claim 1, wherein the propellant is produced by a chemical reaction.

* * * * *

UNITED STATES PATENT AND TRADEMARK OFFICE
CERTIFICATE OF CORRECTION

PATENT NO. : 6,960,184 B2
DATED : November 1, 2005
INVENTOR(S) : Willis et al.

It is certified that error appears in the above-identified patent and that said Letters Patent is hereby corrected as shown below:

Title page,
Item [63], Related U.S. Application Data, should read:
-- Divisional application of application no.: 09/465,573, filed on December 17, 1999, now Patent No.: 6,406,455 --.
Item [60], Related U.S. Application Data, should read:
-- Provisional application no.: 60/112,805, filed on December 18, 1998 --.

Signed and Sealed this

Fourteenth Day of February, 2006

JON W. DUDAS
*Director of the United States Patent and Trademark Office*